United States Patent [19]

Grodberg et al.

[11] Patent Number: 5,039,526

[45] Date of Patent: Aug. 13, 1991

[54] BUCCAL LOZENGE FOR FLUORIDE ION MEDICATION

[75] Inventors: Marcus G. Grodberg, Newton, Mass.; David J. Baylink, Redlands, Calif.

[73] Assignee: Colgate-Palmolive Company, New York, N.Y.

[21] Appl. No.: 509,115

[22] Filed: Apr. 16, 1990

[51] Int. Cl.$^5$ .............................................. A01F 13/00
[52] U.S. Cl. .................................. 424/434; 424/435; 424/488; 424/464
[58] Field of Search ............... 424/434, 435, 606, 676, 424/488

[56] References Cited

U.S. PATENT DOCUMENTS

| | | | |
|---|---|---|---|
| 4,292,299 | 9/1981 | Suzuki | 424/16 |
| 4,572,832 | 2/1986 | Kigasawa | 424/19 |
| 4,764,378 | 8/1988 | Keith | 424/435 |
| 4,859,467 | 8/1989 | Grodberg | 424/606 |
| 4,861,590 | 8/1989 | Grodberg | 424/602 |
| 4,871,786 | 10/1989 | Aasen | 523/113 |

Primary Examiner—Thurman K. Page
Assistant Examiner—D. Gabrielle Phelan
Attorney, Agent, or Firm—Robert Stone; Murray Grill

[57] ABSTRACT

A buccal lozenge medication for providing fluoride ion for the prevention and treatment of bone loss disease. The dosage is a lozenge containing from 20 to 100 milligrams of sodium monofluorophosphate and further including a slow release mechanism for controlling release of the fluoride ion while in the mouth. Up to ten percent of sodium fluoride can be added.

6 Claims, No Drawings

BUCCAL LOZENGE FOR FLUORIDE ION MEDICATION

BACKGROUND OF THE INVENTION

1. Field of the Invention

This invention relates to a sustained release systemic fluoride drug product for treatment or prevention of osteoporosis or other bone disease. More particularly, this invention relates to the use of sodium monofluorophosphate, alone or in combination with another fluorine compound, in a sustained release solid unit dosage form, suitable for use in the treatment and prevention of osteoporosis, alveolar bone loss or other bone diseases where systemic fluoride ion is efficacious.

2. Description of the Prior Art

Fluoride stimulates the activity of bone-forming cells and, together with calcium and phosphate, the two major mineral components of bone is also stored in the bone structure. Fluoride seems to directly stimulate the proliferation of osteoblasts resulting in an increase in bone formation.

U.S. Pat. No. 3,287,219 discloses the oral administration of sodium fluoride to promote bone healing.

The role of fluoride in strengthening the teeth and in imparting acid resistance and preventing caries in dental treatment is well documented. The use of sodium fluoride tablets and liquids for infants and young children in areas where the drinking water is not or is only insufficiently fluoridated is well known. For this purpose, fluoride ion from NaF is administered in dosages of about 0.25 to about 1 mg per day. Representative patents in this area include U.S. Pat. Nos. 3,306,824, 4,265,877 and 4,397,837 (toothpaste). The use of sodium monofluorophosphate (MFP) in dental products, particularly toothpaste products, as an anticaries fluoride additive is also well known and is mentioned in U.S. Pat. No. 4,397,837, cited above. The MFP is slowly metabolized by an intestinal enzyme, MFPase or alkaline phosphatase into free fluoride ion which, in turn, is absorbed into the blood stream, some of the MFP being directly absorbed in the liver and converted therein to F ion.

More recently, the use of NaF or MFP for the treatment of bone disease to promote bone formation and strengthen bone has received wide attention. In fact, although not yet approved for use in the United States, both NaF and MFP products for the treatment and prevention of osteoporosis are available in Europe. thus, Flurexal ® is an enteric coated tablet containing 22 mg sodium fluoride (10 mgF) sold by Zyma SA Nyon Suisse; Tridin ® is a chewable tablet containing 38 mg sodium monofluorophosphate (5 mg F), 500 mg calcium gluconate monohydrate, 500 mg calcium citrate tetrahydrate, 200 mg carboxymethyl cellulose, available from Opfermann Arzneimittel GmbH.

According to the directions for use provided with the medications, Flurexal ® should be taken three times each day, while Tridin ® should be taken one to two tablets three times a day for treatment or one tablet three times a day for prevention of steriod-osteoporosis. In general, the typical recommended dosage for F ion is in the order of from about 30 to 60 mg per day for a human adult.

The literature provided with Tridin ® states that gastric and intestinal irritation is seldom observed. To the same effect, Yngve Ericsson, "Monofluorophosphate Physiology: General Considerations," Caries Res. 17 (Suppl. 1), pages 46–55 (1983), reported that "neither in patients nor in numerous experiments with laboratory workers has any subjective discomfort been recorded with doses up to 30 mg F as MFP." However, in one of the present inventors' own clinical studies and patient evaluations, the occurrence of gastric and intestinal distress was observed in a significant number of cases.

Attempts to solve the adverse side effects of gastrointestinal (GI) tract symptoms by minimizing the availability of F ion in the stomach by providing NaF in a sustained release form have only been partially effective in avoiding GI irritation. More particularly, it has been observed that, while slow release sodium fluoride is well tolerated by approximately 70% of patients, there is adverse gastrointestinal effects in the other approximate 30% of patients.

SUMMARY OF THE INVENTION

The present invention provides a fluoride treatment for osteoporosis, alveolar bone loss and other localized bone disorders which virtually solves the problem of gastric irritation.

Quite surprisingly, in view of the fact that the sustained release type unitary dosage product for administering NaF is only variably effective in avoiding the occurrence of gastric irritation, it has now been discovered that, when MFP is administered in a sustained release form, the occurrence of gastric intestinal irritation is almost totally eliminated.

Accordingly, it is an object of this invention to provide a fluoride ion drug preparation useful in the treatment or prevention of osteoporosis (bone disease) which does not cause adverse GI symptoms, such as gastric irritation.

It is a specific object of this invention to provide a unitary dosage form of MFP which provides sufficient quantities of F ion to be useful in the prevention or treatment of osteoporosis in which the MFP is administered from the unitary dosage product at a slow rate over the course of at least several hours, whereby occurrence of gastric irritation is avoided. The form used for a buccal lozenge, which slowly releases the fluoride ion over a period from two to four hours in which no irritation of the mouth interior occurs and in which there is some application of fluoride ion containing substance applied on the user's dentition. The fluoride enters the bloodstream by way of transmucosal absorption of most of the fluoride ion leaving only sufficient fluoride ion to have a meaningful effect on the dentition with whatever is swallowed in saliva to have no harmful effect on the gastrointestinal tract.

It is another object of the invention to provide a method for treating or preventing osteoporosis by administering, at least once daily, to a patient suffering from or at risk for osteoporosis a solid unitary dosage product containing sufficient amounts of MFP effective for the promotion of, or maintenance of, formation and strengthening for diseased or weakend bone wherein the product includes means for slowly releasing the MFP over the course of at least several hours.

In accordance with these objectives and other objects, which will become apparent from the following description, the present invention provides, in one aspect thereof, a medication for providing fluoride ion for the treatment or prevention of osteoporosis or other bone disease, including alveolar bone loss, which is in the form of a solid unitary dosage lozenge containing from about 20 milligrams (mg) to about 100 mg of sodium monofluorophosphate (Na$_2$PO$_3$F) and further including means for controlling the release of the monofluorophosphate over a period from two or four hours while in the mouth of the user whereby the quantity of fluoride ion present in the stomach at any given time is below the threshold value at which gastric irritation will occur and wherein an effective amount of fluoride ion containing material is applied directly on the teeth of the user.

The sustained release unitary dosage product of this invention may include MFP as the active ingredient. Alternatively, MFP may be used in combination with NaF, or a mixture thereof.

In a specific and preferred embodiment of the invention, the means for controlling release of MFP and any other active ingredient includes a mass of water swellable cellulosic powder forming a coherent fibrous powder network as a matrix in which the monofluorophosphate is uniformly and homogeneously dispersed, whereby, upon introduction of the unitary dosage product into an aqueous medium in the mouth, the cellulosic fibers at the surface of the product soften and loosen from the remaining mass of fibers to thereby release a stream of the monofluorophosphate.

The initial loosening of the fibers causes a very slow release of the fluoride ion for up to four hours, to permit transmucosal passage of the fluoride ion into the bloodstream while allowing sufficient fluoride ion, in the order of five to ten percent of the fluoride ion, to have direct application on the dentition of the user. Saliva may carry another five to ten percent of the fluoride ion into the gastrointestinal tract where there would be not adverse effect.

According to the method aspect of the invention, a patient suffering from or at risk of osteoporosis is treated with at least one of the sustained release unitary dosage MFP products of this invention along or with a calcium ion supplement.

DETAILED DESCRIPTION OF THE INVENTION

Osteoporosis can be broadly defined as increasing weakness and fragility of the bones. It most frequently occurs in elderly, post-menopausal women and in elderly (presenile or senile) men, but also occurs in idiopathic forms. Osteoporosis can also occur in connection with, i.e. as an undersirable side effect of, corticoid treatment (steriod-osteoporosis). Certain localized forms of bone disease may also be associated with a general weakness and fragility of the bone structure due to insufficient new bone formation. Therapeutic indications includes any bone wasting disease, genetic, such as osteogenesis imperfecta, or acquired, such as renal bone disease. Additional use for this product is for the prevention of caries.

One of the effects of advanced periodontal disease is the loss of alveolar bone (i.e. that portion of the jaw bones that support the teeth) mass, which eventually causes loosening and loss of teeth. Alveolar bone loss may also occur after tooth extractions and, in some cases, after the insertion of dental implants.

Bone is composed of an organic phase, collagen and an inorganic crystalline phase of calcium phosphate, or more specifically, hydroxyapatite, Ca$_{10}$(PO$_4$)$_6$(OH)$_2$. Fluoride plays an important role in the prevention of bone loss by stimulating the formation of less soluble fluorapatite Ca$_{10}$(PO$_4$)$_6$F$_2$. Therefore, in osteoporosis, alveolar bone loss and other bone diseases associates with general weakening or loss of the bone tissue, or in cases where the normal dietary intake of calcium is insufficient, a dietary supplement to supply additional calcium is usually appropriate. The addition to the calcium supplement of, or the separate administration of, a source of fluoride ion will, according to recent scientific research, greatly enhance the reversal of bone loss, the fluoride stimulating new bone formation and the calcium being an indispensable building block for bone tissue.

Sodium fluoride and sodium monofluorophosphate can each be used to provide the fluoride ion to be absorbed into the blood for eventual skeletal uptake. Sodium fluoride, NaF, has the advantage that it has a higher F content than sodium monofluorophosphate, MFP. NaF is also more rapidly absorbed, at least in the first few hours, into the blood. However, NaF has higher acute toxicity than MFP and causes stomach or oral cavity irritation in a much higher percentage of patients than does MFP. MFP is compatible with ionizable calcium compounds since Ca(MFP) is about twenty times more soluble than CaF$_2$.

Unfortunately, when ingested orally in a single dosage, typically about 30 to 60 mg F per day for human adults, MFP, although not as pronounced as NaF, also causes stomach irritation.

In accordance with the present invention, it has been found that by incorporating the MFP alone or in combination with a small amount of sodium fluoride, the occurrence of GI irritation can be avoided. Although not wishing to be bound by any particular theory, it is presumed that, by only gradually releasing the MFP from the unitary dosage product, the quantity of fluoride ion present in the mouth or stomach at any given time is below the threshold value at which oral irritation or gastrointestinal irritation will occur. Since a similar alleviation of GI symptoms is not observed for a slow release NaF product, it is further presumed that the more rapid ionization of NaF into sodium and fluorine ions, as compared to the rate of enzymatic hydrolysis of MFP in the stomach, may also account for this different result. In any case, by whatever mode of action, by incorporating the MFP with means for controlling the release of the monofluorophosphate over a period up to a maximum of four hours from the time of placement into the mouth, oral and gastrointestinal irritation will be avoided.

The means for providing controlled (i.e. sustained) release of the active ingredient is the Forest Synchron system.

The preferred controlled-release oral drug delivery system is the Forest Synchron drug delivery system in which the active ingredient, MFP, is dispersed uniformly and homogeneously throughout a mass of water-swellable modified cellulosic powder or fibers forming a coherent network, as a matrix. The mixture of the fibrous or powdery mass and active ingredient(s), with optional additives, such as flavoring, binder, lubricant, processing aids and the like, is compacted into a lozenge which, prior to use, is hard and dry. After the lozenge is placed between the inner cheek and the gum in the mouth and comes into contact with the aqueous oral fluids, including mainly saliva, the outer layer of the lozenge becomes soft and gelatinous, while the inner portions remain dry. At the softened and gelatinous surface, the cellulose powder or fibers become loose and separate from the remaining mass, thereby releasing a portion of the active ingredients. During the period the lozenge remains in the mouth and then travels down through the GI tract, the newly exposed outer surfaces become moistened and in turn become soft and gelatinous to loosen additional cellulosic material, thereby allowing additional amounts of MFP and any dispersed substances to be steadily and generally uniformly released into the mouth and thence into the stomach or intestines. Accordingly, the inserted lozenge will release a stream of the sodium monofluorophosphate, as well as any other active ingredient.

For further details and discussion of the Forest Synchron drug delivery system, reference is made to the following U.S. Patents, the disclosures of which are incorporated hereby by reference thereto: U.S. Pat. Nos. 3,870,790, 4,226,849, 4,357,469, 4,369,172 and 4,389,393, all assigned to Forest Laboratories, Inc.

Typical formulations of a sustained-release unitary dosage lozenge according to the invention which utilizes the Forest Synchron system, in addition to the active ingredient formulation, is shown immediately below:

| Ingredient | Example Amount (milligrams) |
| --- | --- |
| $Na_2$ MFP | 76.0 |
| Ethel Cellulose | 8.0 |
| Hydroxpropylmethylcellulose (Methocel E4M) | 7.0 |
| Hydrogenated Vegtable Oil | 1.0 |
| Sodium salt of naphthalenesulfonic acid-formaldehyde condensate (Tamol N) | 1.0 1.0 |
| Total Content weight | 93. mg |

It is to be noted that flavoring and sweeteners to be used may include sorbital, manitol, xylital, as well as cyclamate saccharin, and aspartate. Small amounts of these may be added to the formulation, if desired.

This formulation provides 10 mg F ion as MFP and is designed to release the MFP in the oral cavity and thence to the gastronitestinal tract slowly four hours after placement in the mouth.

Using existing saliva or assisted by a swallow of a suitable liquid, such as water, the lozenge may thence be swallowed for utilization of any remaining active ingredients, if any.

The amount of MFP can generally be varied over a range of from about 20 mg to about 100 mg MFP per lozenge to provide correspondingly from about 2.5 mg to about 13 mg F per lozenge. Therefore, based on the current recommended dosage for treatment for osteoporosis and related bone diseases, or from about 30 to 60 mg F per day and recommended dosages of, at most, about one-half these levels for prevention of osteoporosis in, for example, post-menopausal women and presenile or senile men, or for prevention of steriod-osteoporosis or alveolar bone loss, total daily dosages of a lozenge two to four times a day will provide the total recommended requirement of fluoride.

The use of sodium monofluorophosphate as the sole fluoride source is preferred. However, if desired, the formulations can include small amounts of NaF in amounts up to about ten percent (10%), such as 5 to 10%, by weight based on the total weight of NaF+MFP can be added to a sustained-release medication. It has been found that the administration of NaF unexpectedly increases alkaline phosphatase enzyme levels in the intestines, thereby enhancing the formation of F from MFP.

What is claimed is:

1. A buccal lozenge medication for providing fluoride ion for the treatment and prevention of bone loss disease including osteoporosis, alveolar bone loss and for application on the teeth, which comprises a solid, unitary dosage lozenge containing from about 20 to 100 milligrams of sodium monofluorophosphate and further containing means for controlling the release of the monofluorophosphate over a period extending up to four hours after placement in the mouth, whereby the quantity of fluoride ions at any given time is below the threshhold value at which oral cavity or gastric irritation will occur and where the major amount of fluoride ion is absorbed transmucosally into the bloodstream.

2. The composition of claim 1, which further comprises up to about 10% by weight of sodium fluoride based on the combined weight of sodium monofluorophosphate and sodium fluoride.

3. The composition of claim 1, wherein the means for controlling release of the monofluorophosphate comprises a mass of water-swellable cellulosic powder or fiber forming a coherent network as matrix in which the monofluorophosphate is uniformly and homogeneously dispersed, whereby, upon introduction of the unitary dosage into an aqueous medium in the mouth, the cellulosic powder or fibers at the surface of the unitary dosage soften and loosen from the remaining mass to thereby release a stream of the monofluorophosphate over the teeth and thence into the gastrointestinal tract.

4. The composition of claim 3, which further comprises sodium fluoride in an amount up to about 10% by weight based on the combined weight of sodium monofluorophosphate and sodium fluoride.

5. The composition of claim 1, including at least up to 10% by weight of a flavoring and sweetener.

6. The composition according to claim 4, including flavoring and sweetener.

* * * * *